United States Patent [19]
Padmapriya et al.

[11] Patent Number: 6,083,976
[45] Date of Patent: Jul. 4, 2000

[54] METHOD OF SYNTHESIS OF DERIVATIVES OF ALOESIN

[75] Inventors: Abeysinghe Padmapriya, Boulder; Kenneth N. Jones, Broomfield, both of Colo.

[73] Assignee: Univera Pharmaceuticals, Inc., Broomfield, Colo.

[21] Appl. No.: 09/228,859

[22] Filed: Jan. 12, 1999

Related U.S. Application Data

[60] Provisional application No. 60/071,204, Jan. 12, 1998.
[51] Int. Cl.$^7$ ........................ A61K 31/352; C07D 311/22
[52] U.S. Cl. ........................ 514/456; 549/401; 536/1.11; 514/23
[58] Field of Search ........................ 549/401; 536/1.11; 514/23, 456

[56] References Cited

U.S. PATENT DOCUMENTS

| | | | |
|---|---|---|---|
| 5,552,436 | 9/1996 | Clemente et al. | 514/456 |
| 5,587,176 | 12/1996 | Warren et al. | 424/443 |
| 5,801,256 | 9/1998 | Padmapriya et al. | 549/401 |

FOREIGN PATENT DOCUMENTS

96/40182  12/1996  WIPO.

OTHER PUBLICATIONS

Speranza, G. et al.: A C–glucosylated 5–methylchromone from Kenya aloe. Phytochemistry, vol. 25, pp. 2219–2222, 1986.
Hart et al. (1988) J. of Ethnopharmacology 23:61–71.
Hirata and Suga (1977) Z. Naturforsch 32c:731–734.
Holdsworth (1972) *Chromones in Aloe Species, Part I—Aloesin* PM 19(4):322–325.
Grindlay and Reynolds (1986) J. of Ethnopharmacology 16:117–151.
Yagi et al. (1987) Plant Medica 515–517.

*Primary Examiner*—Alan L. Rotman
*Assistant Examiner*—Charanjit S. Aulakh
*Attorney, Agent, or Firm*—Swanson & Bratschun LLC

[57] ABSTRACT

The present invention discloses a method for the synthesis of derivatives of aloesin, alkylated at the C-7 hydroxyl group. The present invention includes the modified aloesins produced by the method of this invention and the use of these compounds as skin whitening agents.

9 Claims, No Drawings

METHOD OF SYNTHESIS OF DERIVATIVES OF ALOESIN

RELATED APPLICATIONS

This application claims priority from United States Provisional Patent Application Serial No. 60/071,204, filed Jan. 12, 1998, entitled "Octylaloesin, A Skin Whitening Agent and Its Synthesis."

FIELD OF INVENTION

The present invention relates generally to a method for the synthesis of derivatives of aloesin, a C-glucosylated 5-methylchromone obtained from Aloe. Specifically, the present invention relates to a method for the synthesis of derivatives of aloesin, alkylated at the C-7 hydroxyl group. The present invention also includes the modified aloesins produced and the use of these compounds as skin whitening agents.

BACKGROUND OF THE INVENTION

There is a world-wide demand for products able to inhibit or prevent excessive pigmentation of the skin. Melanin, the skin's natural pigment, is synthesized in the melanocytes in varying concentrations, depending on skin type (genetic disposition) and environmental effects. Melanocytes are cells which occur in the basal membrane of the epidermis, and account for between 5% and 10% of the cellular content (approximately 1200–1500 melanocytes per $cm^2$). Melanocytes are stimulated by ultraviolet (UV) light, producing greater quantities of melanin. The melanin is then transported into the keratinocytes, where it becomes visible as a brown skin color.

The number of melanocytes in human skin is more or less the same, irrespective of skin color. The color of the skin is largely dependent on the quantity and type of melanin produced (black eumelanin or yellow to reddish-brown pheomelanin). Asians and light-skinned people have lower levels of eumelanin than dark-skinned people, and correspondingly less protection against the effects of radiation. People with red hair are characterized by pigmentation with pheomelanin, and have little or no photo-protection. Additionally, the distribution of melanin in the skin also varies. In people with light skin, the greater part of the pigment lies in the basal layer, whereas in those with dark skin, the melanin is spread throughout, reaching into the horny layer.

Tyrosinase is the key enzyme in the synthesis of melanin. It has been determined that tyrosinase needs both the substrate and divalent metal ions for its catalytic activity. The processes presently used for inhibiting the synthesis of melanin with a view to lightening skin are based on substances which interact directly with the tyrosinase, or indirectly regulate its activity, e.g., by complexing the necessary metal ions.

To date, the best-known active substance for de-pigmentation is hydroquinone, a bleaching agent. Hydroquinone, however, does not inhibit melanin biosynthesis, rather it bleaches existing melanin. If applied over long periods of time, hydroquinone can have serious side effects, which has led to its being permitted only in limited concentrations in some countries, and to its being completely forbidden for applications in cosmetic products in other countries. Furthermore, hydroquinone leads to permanent de-pigmentation, and thus to increased photosensitivity of the skin when exposed to UV light.

Better tolerated skin lightening substances currently being used are of natural origin, e.g., arbutin (from the leaves of the common bearberry, *Uvae ursi*), liquorice extract (from liquorice root), ascorbic acid (vitamin C from citrus fruits) and their derivatives, as well as kojic acid (from carbohydrate solutions under the effect of certain bacteria) (see Kobayashi et al. (1995) BioSci. Biotech. Biochem. 59:1745). These substances, which are highly soluble in water, act on the tyrosinase as competitive inhibitors; however, they are unstable in some formulations, and have the disadvantage that only very small quantities penetrate the deeper skin layers and reach the melanocytes in the basal membrane. A further disadvantage of these substances is their low level of efficacy, which necessitates their being used in high concentrations. Compared to the quantity of hydroquinone used, 17 times as much ascorbic acid and over 100 times as much arbutin is required to achieve a similar effect.

Gombert describes two cosmetic products for lightening skin, both of which are produced from plants. (Gombert (1997) Cosmetics and Toiletries Manufacture Worldwide, pp.151–157). Both products contain a mixture of several competitive tyrosinase inhibitors in an aqueous solution, emulsified into creams. An in vitro enzyme test was carried out, in which it was possible to show that the substances used had an efficient inhibitory effect; however with in vivo tests, it was not until a cream with a 10% active ingredient content had been applied for at least 42 days that a demonstrable de-pigmentation of the skin occurred. In one test involving ten people using a cream with a 3% active ingredient content, proof of any positive effect at all could only be found with two people. It is specifically pointed out that, since the natural substances used in the formulation are extremely unstable, strong antioxidants must be added to the formulation. Also, if the finished formulations are stored at temperatures below 15° C., the substances can crystallize.

Lee and Kim (Cosmetics and Toiletries 110:51–56, October 1995), describe a substance isolated from the bark of the roots of the mulberry bush *Broussonetia papyrifera*, which acts as a free radical scavenger. As the formation of melanin, referred to as melanogenesis, is increased by the presence of free radicals in the skin, it can be reduced with the help of a free radical scavenger of this type. The subject of this article is not the de-pigmentation of skin, but rather the suppression of melanogenesis with the help of a free radical scavenger. Furthermore, it takes, over 40 days for the described effect to occur. In this paper also, attention is drawn specifically to the instability of the active substances in the formulation.

Aloe is an intricate plant which contains many biologically active substances. (Cohen et al. in *Wound Healing/Biochemical and Clinical Aspects*, 1 st ed. WB Saunders, Philadelphia (1992)). Over 300 species of Aloe are known, most of which are indigenous to Africa. Studies have shown that the biologically active substances are located in three separate sections of the aloe leaf—a clear gel fillet located in the center of the leaf, in the leaf rind or cortex of the leaf and in a yellow fluid contained in the pericyclic cells of the vascular bundles, located between the leaf rind and the internal gel fillet, referred to as the latex. Historically, Aloe products have been used in dermatological applications for the treatment of burns, sores and other wounds. These uses have stimulated a great deal of research in identifying compounds from Aloe plants that have clinical activity, especially anti-inflammatory activity. (See, e.g., Grindlay and Reynolds (1986) J. of Ethnopharmacology 16:117–151; Hart et al. (1988) J. of Ethnopharmacology 23:61–71). As a result of these studies there have been numerous reports of Aloe compounds having diverse biological activities, including anti-tumor activity, anti-gastric ulcer, anti-diabetic, anti-tyrosinase activity (see, e.g., Yagi et al. (1977) Z. Naturforsch 32c:731–734) and antioxidant activity (see, International Application Serial No. PCT/US95/07404).

Yagi et al. disclose a group of compounds isolated from Aloe, particularly aloesin and one of its derivatives, 2"-O-feruloylaloesin, which are effective inhibitors of tyrosinase. (Yagi et al (1987) Plant Medica 515–517). Biochemical testing of the enzyme inhibition by means of the Lineweaver Burk diagram showed that these substances are non-competitive inhibitors of tyrosinase. Aloesin is a C-glucosylated 5-methylchromone obtained from the leaves of Kenya Aloe sp., having the following chemical structure and conventional numbering:

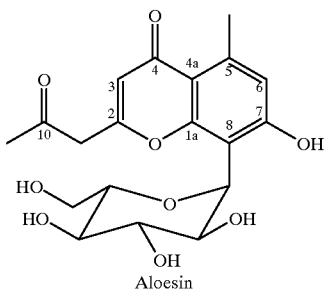

Aloesin (Holdsworth (1972) Chromones in Aloe Species, Part I-Aloesin PM 19(4):322–325). In vitro, aloesin is a strong inhibitor of tyrosinase activity (Yagi et al. (1987) Planta Medica 515–517). In assays of tyrosinase activity on the substrate L-DOPA, aloesin is capable of 50% inhibition at a concentration of 0.2 mM. Aloesin, however, is soluble in water, which limits its ability to be retained on the stratum corneum of the skin, and consequently reduces its effectiveness as a cosmetic agent. There is no disclosure of the inhibitors being applied in in vivo tests. It would be desirable to modify aloesin in such a way that the compound becomes more fat soluble while retaining potent tyrosinase inhibitory activity.

SUMMARY OF THE INVENTION

The present invention includes a novel method for the synthesis of derivatives of aloesin, a C-glucosylated 5-methylchromone isolated from Aloe. Specifically, the present invention includes a method for the synthesis of derivatives of aloesin, alkylated at the C-7 hydroxyl group. The method of this invention comprises reacting aloesin with a substituted or unsubstituted alkane containing a leaving group in the presence of a base. In a preferred embodiment the leaving group is a halogen. In the most preferred embodiment the leaving group is iodine and the base is sodium carbonate.

The present invention also includes the modified aloesins produced by the method of this invention and the use of these compounds as skin whitening agents. The alkylated aloesins, produced by the method of this invention have the functionality of aloesin, a tyrosinase inhibiting compound with skin whitening activity, but have greater biological activity than aloesin as indicated by in vitro tyrosinase assays. Additionally, the alkyl group makes the derivatized aloesins more fat soluble than aloesin, allowing them to be retained in the stratum corneum of the skin more effectively than aloesin. As a result, the alkylated aloesins are more potent and faster acting skin lightening agents than aloesin.

DETAILED DESCRIPTION OF THE INVENTION

The present invention includes a method for the synthesis of derivatives of aloesin, a C-glucosylated 5-methylchromone isolated from Aloe. Specifically, the present invention includes a method for the synthesis of derivatives of aloesin, alkylated at the C-7 hydroxyl group. The method of this invention comprises reacting aloesin with a substituted or unsubstituted alkane containing a leaving group in the presence of a base. The general reaction scheme of the present invention can be illustrated as follows:

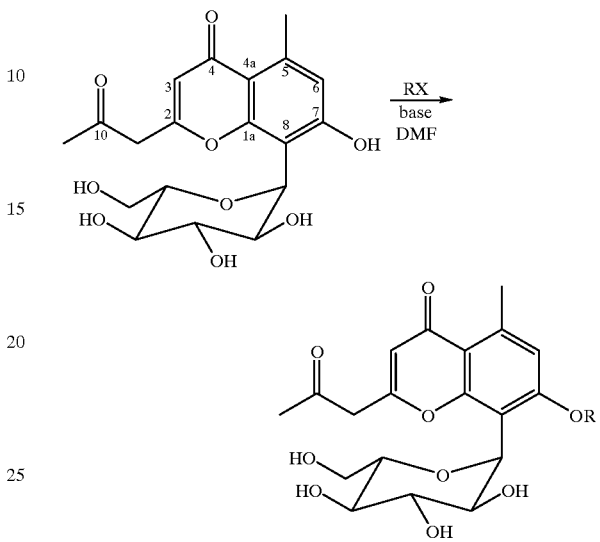

wherein
R is selected from a substituted or unsubstituted C1–C8 alkyl group; and
X is a leaving group, including but not limited to, a halogen selected from the group consisting of
Cl, Br or I. X, however, can be selected from any other leaving group known in the art.

In a preferred embodiment X is I and the base is sodium carbonate.

Example 1 illustrates the general method of this invention using both iodo- and bromooctane. As provided above, the iodo alkane is the preferred reagent and was used to produce the modified aloesins of Table 1.

Example 2 illustrates the general method for determination of tyrosinase inhibition by the alkylated aloesins, using octylaloesin for purposes of illustration. Aloesin exhibits 50% tyrosinase inhibition at an average concentration of 0.2500 mM in this assay. Octylaloesin exhibits 50% tyrosinase inhibition at an average concentration of 0.1074 mM. Thus, octylaloesin is approximately 2.3 fold more potent as a tyrosinase inhibitor than aloesin.

The following examples are provided for illustrative purposes only and are not intended to limit the scope of the invention.

EXAMPLES

Example 1

Method of Synthesis of Aloesin Derivatives

1-Iodooctane. A solution of aloesin (123 g; which was dried for four days under high vacuum prior to use) in anhydrous DMF (700 mL) was stirred with 3 Å molecular sieve (MS) (105 g), sodium carbonate (125 g) and iodooctane (60 mL) for five days at room temperature, under nitrogen. The reaction mixture was centrifuged and the liquid layer was decanted. The solid residue was then washed with DMF (200 mL). The combined DMF layer was concentrated by rotary evaporation under high vacuum. The residue was partitioned between EtOAc and water (1 L each). The ethyl acetate layer was dried over sodium sulfate and concentrated by rotary evaporation. The residue was then purified by flash column chromatography on silica gel using 6% methanol in chloroform to obtain octylaloesin (64.97 g; 41.4%) as a light yellow solid. 1-Bromooctane. Aloesin ($C_{19}H_{22}O_9$, MW=394.366, 0.1 g) obtained from Aloe was dissolved in 1 mL of dry N,N-dimethylformamide (DMF). To this solution was added NaH powder (6 mg) and the mixture was stirred for 1 hour at room temperature. Into this mixture was added 45 μL of 1-bromooctane, and the mixture was stirred for 4 hours at room temperature. The reaction mixture was then poured into 10 ml of water, and extracted twice with 10 ml of ethyl acetate. The ethyl acetate layer was dried over $MgSO_4$ and concentrated by rotoevaporation to obtain the crude product as an oil. This was then passed over silica gel using 14% methanol in dichloromethane to obtain 18 mg of octylaloesin ($C_{27}H_{38}O_9$, $M_W$=506.574) as a light yellow solid. The yield was approximately 14%.

The same general procedure was employed to make a variety of additional alkyl aloesin derivatives. Table 1 sets forth the product and yield of these syntheses using methyl, ethyl and butyl iodide.

TABLE 1

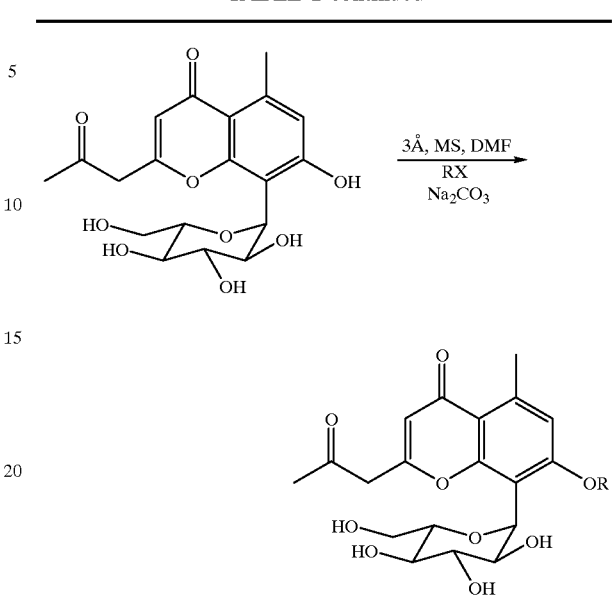

| RX | Product | Yield |
|---|---|---|
| MeI | Methylaloesine | 53% |
| EtI | Ethylaloesin | 19.1% |
| BuI | Butylaloesin | 10.5% |
| OctylI | Octylaloesin | 41.4% |

Example 2

Tyrosinase Inhibition by Octylaloesin

A tyrosinase activity assay was performed using L-DOPA as a substrate. Each 750 μL assay mixture contained $KH_2PO_4/K_2HPO_4$ at a concentration of 50 mM, L-DOPA at a concentration of 0.4 mM, 48 U of tyrosinase activity (tyrosinase obtained from SIGMA at 4,400 U/mg), and varying concentrations of the inhibitor being tested. The progress of the reaction was monitored by measuring the absorbance of the reaction mixture at 475 nm.

What is claimed is:

1. A method for the preparation of aloesin, alkylated at the C-7 hydroxyl group comprising reacting aloesin with a substituted or unsubsituted alkyl group containing a leaving group in the presence of a base.

2. The method of claim 1 wherein the leaving group is a halogen selected from the group consisting of Br, Cl or I.

3. The method of claim 1 wherein the leaving group is I and the base is $Na_2CO_3$.

4. The method of claim 1 wherein the alkyl group is selected from the group consisting of C1–C8 carbon atoms.

5. A composition of matter produced by the method of claim 1.

6. A compound of the formula:

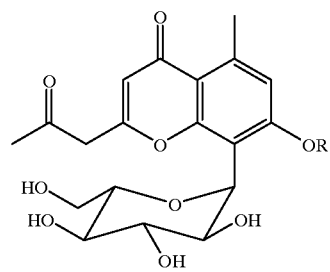

wherein R is selected from the group consisting of a substituted or unsubstituted C2–C8 alkane, branched or straight chain.

7. The compound of claim 6 wherein R is selected from the group consisting of —$CH_2CH_3$, —$(CH_2)_2CH_3$, isopropyl, —$(CH_2)_3CH_3$, sec-butyl, —$(CH_2)_4CH_3$, —$(CH_2)_5CH_3$, —$(CH_2)_6CH_3$ and —$(CH_2)_7CH_3$.

8. A method for the reversible de-pigmentation of the skin comprising, topically applying an effective amount of a composition comprising a compound produced by the method of claim 1.

9. A method for the reversible de-pigmentation of the skin comprising, topically applying an effective amount of a composition comprising a compound of claim 6.

* * * * *